United States Patent [19]

Rane et al.

[11] Patent Number: 4,468,404

[45] Date of Patent: Aug. 28, 1984

[54] 3-ARALKYLOXY-2,3-DIHYDRO-2-(TRIAZOLYMETHYL)BENZO(B)THIOPHENES

[75] Inventors: Dinanath F. Rane, Emerson, N.J.; John J. Wright, Evansville, Ind.; Russell E. Pike, Stanhope, N.J.

[73] Assignee: Schering Corporation, Kenilworth, N.J.

[21] Appl. No.: 403,275

[22] Filed: Jul. 29, 1982

Related U.S. Application Data

[63] Continuation-in-part of Ser. No. 215,948, Dec. 12, 1980, Pat. No. 4,352,808.

[51] Int. Cl.³ .................. A01N 43/64; A01N 43/78; C07D 405/06; C07D 409/06
[52] U.S. Cl. .................. 424/269; 424/250; 424/263; 424/270; 424/258; 544/366; 544/369; 546/153; 546/172; 546/176; 546/269; 546/274; 548/186; 548/189; 548/262
[58] Field of Search .......... 548/262, 186, 189; 424/269, 263, 250, 258; 544/366, 369; 546/276, 269, 274, 153, 172, 176

[56] References Cited

U.S. PATENT DOCUMENTS 3,927,018 12/1975 Houlihan .................. 424/273 R
4,352,808 10/1982 Rane et al. .................. 424/258

FOREIGN PATENT DOCUMENTS 1445707 8/1976 United Kingdom .................. 548/341

*Primary Examiner*—Alton D. Rollins
*Attorney, Agent, or Firm*—Anita W. Magatti

[57] ABSTRACT

3-Aralkyloxy-2,3-dihydro-2-(triazolylmethyl)benzo(b)-thiophenes and related derivatives having antifungal, antibacterial, and antiprotozoal activity are prepared by the reaction of the corresponding 2,3-dihydro-3-hydroxy-2-(triazolylmethyl)benzo(b)thiophene or related derivative and an aralkyl halide.

Preferred compounds are those where the aralkyl function is a hetercyclic aromatic, particularly 2-chloro-3-thenyl, and where the benzene nucleus is substituted by chlorine or fluorine.

Pharmaceutical formulations comprising compounds of this invention are described, as well as the method for their use in treating microbial infections.

15 Claims, No Drawings

3-ARALKYLOXY-2,3-DIHYDRO-2-(TRIAZOLYMETHYL)BENZO(B)THIOPHENES

FIELD OF INVENTION

This application is a continuation-in-part of Ser. No. 215,948, filed Dec. 12, 1980 now U.S. Patent 4,352,808.

This invention relates to novel 3-aralkyloxy-2,3-dihydro-2-(triazolymethyl)benzo(b)thiophenes and related derivatives which exhibit antifungal, antibacterial, and antiprotozoal activity, pharmaceutical compositions comprising said 3-aralkyloxy-2,3-dihydro-2-(triazolylmethyl)benzo(b)thiophenes and derivatives, and to methods for their use in treating fungal, bacterial or protozoal infection.

In particular, this invention relates to 3-aralkyloxy-2,3-dihydro-2-[(1',2', 4'-triazolyl)-(1' or 4')-methyl]benzo(b)thiophenes and the corresponding 4-aralkyloxy-3-[(1',2',4'-triazolyl)-(1' or 4')-methyl] thiochromans.

This invention also relates to pharmaceutical compositions comprising said 3-aralkyloxy-2,3-dihydro-2-(triazolymethyl)benzo(b)thiophenes and related derivatives, and to the method of using said pharmaceutical compositions to elicit an antimicrobial (i.e., antibacterial, antifungal or antiprotozoal) response in a warm blooded animal having a susceptible microbial (i.e., bacterial, fungal or protozoal) infection.

GENERAL DESCRIPTION OF THE INVENTION COMPOSITION-OF-MATTER ASPECT

Included among the antimicrobially active compositions-of-matter of this invention are compounds of the formula I:

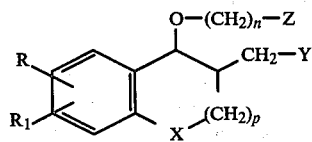

wherein
n is 0 to 4;
p is 0 to 1;
R and $R_1$ are independently hydrogen, lower alkyl, halogen, halogenated lower alkyl, nitro, or amino groups;
X is sulfur, sulfinyl or sulfonyl;
Y is 1,2,4-triazolyl, or lower alkyl and aryl derivatives of the foregoing, said aryl being a member selected from the group consisting of phenyl, halophenyl, and loweralkylphenyl;
Z is a member selected from the group consisting of alkyl, alkenyl, alkynyl, cycloalkyl, and heterocyclic aromatic groups and the lower alkyl and halogen substituted derivatives thereof, provided that when n is 0, Z is not 1-alkynyl; and where n is 1 to 4, Z is also a member selected from the group consisting of phenyl, phenyl substituted by lower alkyl, halogen, or N(N'-alkanoylpiperazine), alkoxy, alkylthio, aryloxy, and arylthio;
and the pharmaceutically acceptable acid addition salts thereof.

As used in the specification and claims, the term "halogen" refers to fluorine, chlorine, bromine and iodine. "Lower alkyl" refers to hydrocarbon chains of 1 to 4 carbon atoms, for example methyl, ethyl, n-propyl, iso-propyl, or t-butyl groups.

Included among the substituents contemplated for the moiety "Z" are alkyl groups, straight or branched, of 1 to 10 atoms, examples of which include the aforementioned lower alkyl groups, plus n-butyl, t-butyl, n-pentyl, n-hexyl, 2-ethylpentyl, and t-decyl groups; alkoxy groups having 1-10 carbon atoms, including methoxy, ethoxy, propoxy, and decyloxy; thioalkyl groups having 1-10 carbon atoms, i.e. methylthio, ethylthio, decylthio; cycloalkyl groups having 3-6 carbons, including cyclopropyl, cyclobutyl, cyclopentyl, and cyclohexyl; alkenyl groups including straight or branched chains of 3 to 10 carbons, including 1-propenyl, 2-propenyl, 2-pentenyl, 3-hexenyl, 5-octenyl, and 2-decenyl; and alkynyl groups including straight or branched chains having 3-10 carbons, for example propynyl, 2-butynyl, 2-pentynyl and 5-decynyl.

Also included for the moiety "Z" are groups such as phenyl substituted by lower alkyl, halogen, or N-(N'-alkanoylpiperazine) e.g. mono-, di-, and trihalogenophenyls, mono-, di-, and tri-lower alkylphenyl, and the 1-acetyl-4-piperazinylphenyl group; aryloxy and arylthio groups wherein aryl refers to phenyl and halogeno- and lower alkyl-substituted phenyl, e.g. mono-, di-, and tri-lower alkylphenyl and mono-, di-, and trihalogenophenyl such as 4-chlorophenyl, 2,4-dicholorophenyl, 2,6-dichlorophenyl, 2,4,6-trichlorophenyl, tolyl, xylyl, and mesityl.

The alkanoyl groups contemplated in the term "N-(N'-alkanoylpiperazine)" are residues of straight or branched chain alkanoic acids having up to 6 carbon atoms, for example formyl, acetyl, or butyryl.

Aromatic heterocyclic groups contemplated for the moiety "Z" are unsaturated ring systems containing at least one hetero atom selected from the group consisting of O, S, and N and 3 to 10 carbons in a single or fused ring system which may be substituted by halogen or lower alkyl groups, such as 2-thienyl, 3-thienyl, 2-chloro-3-thienyl, 5-chloro-2-thienyl, 2,5-dichloro-3-thienyl, pyridyl, quinolyl, thiazolyl, and furanyl.

Of the compounds of formula I, preferred are those where X is sulfur and p is 0, i.e. compounds of the following formula II, particularly the cis isomer:

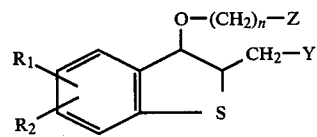

wherein $R_1$, $R_2$, Y, Z, and n are as defined in formula I. Of the compounds of formula II, particularly valuable are those where Z is a substituted phenyl or heterocyclic aromatic group. Of these, particularly preferred are compounds where Z is thienyl and Y is 1,2,4-triazolyl, e.g. cis-6-chloro-3-(2'-chloro-3'-thenyloxy)-2,3-dihydro-2-[(1'',2'',4''-triazolyl)-1''-methyl]benzo(b)thiophene and cis-6-chloro-3-(2'-chloro-3'-thenyloxy)-2,3-dihydro-2-[(1'',2'',4''-triazolyl)-4''-methyl]benzo(b)thiopene.

Compounds of formula I can exist in two isomeric forms, i.e. when p is 1, cis-3,4 or trans-3,4, and when p is 0, cis-2,3 or trans-2,3. Both forms are within the inventive concept as defined by formulae I and II, as are the individual optical isomers.

Also included within the composition-of-matter aspect of this invention are pharmaceutically acceptable acid addition salts of the compounds defined by formula I, which salts are made according to known procedures such as by neutralizing the free base with the appropriate acid, usually to about $p$H5. Suitable acids for this purpose include acids such as hydrochloric, sulfuric, phosphoric, hydrobromic, nitric and the like.

Compounds of this invention where X is sulfur are prepared by reacting substituted hydroxyl compounds of the formula III

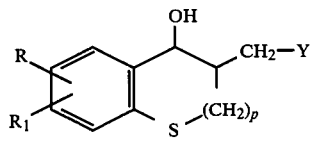

in which R, $R_1$, Y, and p have the meanings given above, with an alkali metal base and with a halide $Z(CH_2)_nA$, in which Z and n are as defined above and A is a halogen atom, to give a compound of formula I. If desired, the resulting compound is converted into a pharmaceutically acceptable acid addition salt.

The reaction of a compound of the general formula III with an alkali metal base (for example an alkali metal hydride, alkali metal hydroxide, alkali metal amide or alkali metal alcoholate) and with a halide, $Z(CH_2)_nA$, is carried out in an organic solvent, for example dimethylformamide, hexamethylphosphoric acid triamide, an aromatic hydrocarbon (e.g., benzene or toluene), an ether (e.g., diethyl ether, dioxane, tetrahydrofuran or ethylene glycol dimethyl ether), a lower alcohol, or a ketone (e.g., acetone) at a temperature within the range of 0°–100° C., and preferably within the range from 20°–60° C.

In order to increase the yield, the alkali metal base and the halide may be used in excess.

In a preferred method of preparation of compounds of formula I where X is sulfur, such as disclosed in Example 1 or 2, sodium hydride is added to a solution of a hydroxyl compound of formula III in dimethylformamide at 0°–5° C., then allowed to react at room temperature for 1 hour, followed by the addition of the halide $Z(CH_2)_nA$ and reaction for another hour at room temperature. The compound of formula I thereby produced is isolated and purified utilizing known techniques such as extraction, chromatography, and recrystallization.

Compounds of formula I wherein X is SO or $SO_2$ are prepared from compounds wherein X is sulfur, using oxidative procedures known in the art.

The halide starting materials, $Z(CH_2)_nA$, are generally known in the art or are made by procedures well known in the art. Typical halides useful in our procedure are n-hexyl chloride, allyl chloride, propargyl chloride, cyclopropylmethyl chloride, methoxymethyl chloride, methythiomethyl chloride, p-chloro-phenoxymethyl chloride, p-chloro-phenylthiomethyl chloride, and 1-[(4'-(1''-acetyl-4''-piperazinyl)) phenoxy]-2-bromoethane.

Similarly, the starting materials for compounds of formula III where X is sulfur may be made by one of the following sequences of reactions, utilizing techniques known in the art:

(a) a thiochroman-4-one substituted in the benzene nucleus with R functions as defined for formula III is first converted to the corresponding bromoketone by reaction with bromine in a solvent such as ether, chloroform, or carbon tetrachloride. The bromoketone thereby formed is then converted to the corresponding bromohydrin by reaction with a reducing agent, for example, sodium borohydride, in a solvent such as a lower alcohol. The resulting bromohydrin is reacted with 1,2,4-triazole or a substituted 1,2,4-triazole in a solvent such as dimethylformamide, hexamethylphosphoric acid triamide, a lower alcohol or acetonitrile to give a compound of formula III.

(b) An aqueous solution of 1,2,4-triazole or a substituted 1,2,4-triazole is reacted with a 3-dimethylaminomethyl-thiochroman-4-one to form the corresponding [(1',2',4'-triazolyl)-1'-methyl]thiochroman-4-one which, upon reduction with a reducing agent such as sodium borohydride produces a compound of formula III as an isomeric mixture of cis and trans forms. The product may be used as a mixture or separated via conventional techniques (usually chromatography such as described in Preparation 2) to obtain the cis and trans forms free from any co-produced isomer. This procedure is a preferred method of producing compounds where p is 1.

GENERAL DESCRIPTION OF PHARMACEUTICAL COMPOSITION AND METHOD-OF-USE ASPECTS OF THE INVENTION

The present invention includes within its scope the method of eliciting an antifungal, antibacterial, or antiprotozoal response in a host object containing or subject to attack by fungi, bacteria or protozoa which comprises subjecting said host object to an antifungally, antibacterially, or antiprotozoally effective amount of a 3-aralkyloxy-2,3-dihydro-2-[(1'',2'',4''-triazolyl)-(1'' or 4')-methyl](b)thiophene or related derivatives of formula I.

The compounds of formula I exhibit antifungal activity against human and animal pathogens such as the following: *Aspergillus, Candida, Epidermophyton, Geotrichum, Microsporum, Monosporium, Pityrosporum, Rhodotorula, Saccharomyces, Trichophyton, Trichosporon,* and *Torulopsis,* and against protozoal pathogens such as *Trichomonas.*

Additionally, antibacterial activity is exhibited by compounds of formula I against human and animal pathogens such as the following: *Actinomyces, Bacillus, Bacteriodes, Clostridium, Escherichia, Mycobacterium, Nocardia, Propionibacterium, Sarcina, Staphylococcus, Streptococcus,* and *Streptomyces.*

The compounds of formula I also exhibit activity against fungi of primarily agricultural significance, such as the following: *Cladosporium, Colletotrichum, Erysiphe, Fusarium, Helminthosporium, Penicillium, Peronospora, Phytophthora, Pithomyces Polyspora, Puccina, Rhizoctonia, Sclerotium, Uromyces,* and *Venturia,* and against bacteria of primarily agricultural significance, such as: *Agrobacterium, Erwinia,* and *Xanthemonas.*

As discussed hereinabove, the preferred compounds of this invention, i.e. those of formula II, are particularly valuable as antifungal agents as demonstrated by in vivo tests in animals, e.g. a hamster *Candida* infection model, a guinea pig dermatophyte infection model and a mouse systemic *Candida* infection model. These tests indicate the compounds of this invention to be broad-spectrum antifungal agents active topically, orally and parenterally against topical dermatophyte and vaginal and systemic yeast infections.

In general, the dosage of compounds of formula I employed to combat a given fungal infection is similar to the dosage requirements of miconazole, clotrimazole, and ketoconazole, though the particular dosage level and the mode of administration will vary according to the particular host and the type and severity of the infection.

Also included in our inventive concept are pharmaceutical formulations comprising an antifungally, antibacterially or antiprotozoally effective amount of a compound of formula I in a pharmaceutically acceptable, non-toxic carrier for topical, oral or parenteral use.

Topical pharmaceutical dosage forms may be prepared according to procedures well known in the art, and may contain a variety of ingredients. The formulations for topical use include ointments, creams, lotions, powders, aerosols and sprays. Of these, ointments, lotions and creams may contain water, oils, fats, waxes, polyesters, alcohols, or polyols, plus such other ingredients as fragrances, emulsifiers and preservatives. Powders are made by mixing the active ingredient with a readily available, inert, pulverous distributing agent, such as talcum, calcium carbonate, tricalcium phosphate, or boric acid. Aqueous suspensions of the above powders may also be made. Solutions or emulsions may also be prepared using inert solvents which are preferably nonflammable, odorless, colorless, and non-toxic, for example vegetable oils, isopropanol, dimethyl sulfoxide, hydrogenated naphthalenes, and alkylated naphthalenes. Similarly, aerosol or non-aerosol sprays may be prepared using solutions or suspensions in appropriate solvents, e.g. difluorodichloromethane for aerosols.

In the case of topical formulations, e.g. ointments, creams, lotions, powders, or sprays, the formulation will contain about 0.1 to 3 grams of compound of formula I per 100 grams of carrier.

Oral dosage forms include tablets, capsules, elixirs, suspensions, and the like. Tablets contain such excipients as starch or lactose; liquid forms may contain coloring or flavoring agents.

Parenteral forms to be injected intavenously, intramuscularly, or subcutaneously are usually in the form of a sterile solution, and may contain salts or glucose to make the solution isotonic.

In addition to pharmeceutical uses, the compounds of this invention also have agricultural and industrial significance. In agricultural applications, the compounds may be applied directly to plants or soil. The carriers may be powders, such as talc, mica, or clay, or sprays, such as aqueous solutions with or without a solid carrier and a wetting agent. Industrially, the compounds may be used to disinfect glassware, medical equipment, and the like, by rinsing, contacting or impregnating the infected surface with compound in a suitable carrier. Additionally, the compounds may be used to prevent growth of fungi in paints.

The following formulation exemplifies a typical dosage form in which the antimicrobial agents of the invention may be employed. The active ingredient is designated by the term "Drug" which is meant to indicate the following compound: cis-6-chloro-3-(2'-chloro-3'-thenyloxy)-2,3-dihydro-2-[(1″,2″,4″-triazolyl)-1'-methyl]benzo(b)thiophene; It will be appreciated, however, that this compound may be replaced by equally effective quantities of other compounds defined by formula I.

| Cream | Amounts in (mg) | | |
|---|---|---|---|
| | A | B | C |
| Drug | 0.5 | 5.0 | 10.0 |
| Sorbitan Monostearate | 20.0 | 20.0 | 20.0 |
| Polysorbate 60 | 15.0 | 15.0 | 15.0 |
| Spermaceti Synthetic | 30.0 | 30.0 | 30.0 |
| Cetostearyl Alcohol | 100.0 | 100.0 | 100.0 |
| Octyl Dodecanol | 135.0 | 135.0 | 135.0 |
| Benzyl Alcohol | 10.0 | 10.0 | 10.0 |
| Purified Water | to make 1 gram | 1 gram | 1 gram |

Procedure:

Heat the sorbitan monostearate, 95% of the polysorbate 60, synthetic spermaceti, cetostearyl alcohol, and octyl dodecanol to 70° C. Dissolve the benzyl alcohol in 90% of the purified water heated to 75° C. Add the aqueous solution to the melted waxes and stir while cooling to 40° C. Dissolve the remaining portion of the polysorbate 60 in the remaining portion of water, add the drug and pass the slurry through a colloid mill. Add the slurry to the wax mixture and mix until cool.

PREPARATION 1

Cis-2,3-Dihydro-3-Hydroxy-2-[(1',2'4'-Triazolyl)-(1' or 4')-Methyl]Benzo (b)Thiophenes (A) Cis-6-Chloro-2,3-Dihydro-3-Hydroxy-2-[(1',2',4'-Triazolyl-(1' or 4')-Methyl]Benzo(b)Thiophene (1) 3-Bromo-7-Chlorothiochroman-4-One Dissolve 7-chlorothiochroman-4-one (10 gms., 50.3 mmols) in chloroform (100 ml.) and cool the solution to 0°–5° C. Add bromine (2.60 ml., 50.3 mmols) dropwise over a 10-minute period. Stire the reaction mixture at room temperature for one hour, then add chloroform (100 ml.) and extract with 10% aqueous sodium sulfite (100 ml.) followed by water (200 ml.). Dry the chloroform solution over anhydrous magnesium sulfate, filter and evaporate in vacuo to a residue. Recrystallize the residue from cyclohexane to give 3-bromo-7-chlorothiochroman-4-one, m.p. 109°–110° C.

(2) 3-Bromo-7-Chlorothiochroman-4-01

Suspend 3-bromo-7-chlorothiochroman-4-one (59.6 gms., 215 mmols) in methanol (500 ml.), cool to 0.5° C., and with stirring add sodium borohydride (8.18 gms., 215 mmols) in three portions. Continue stirring the reaction mixture at room temperature for three hours, then pour into ice water (4 liters) and extract with chloroform (2 liters). Dry the chloroform solution over anhydrous magnesium sulfate, filter and evaporate in vacuo to a residue. Triturate the residue with chloroform/hexane to give 3-bromo-7-chlorothiochroman-4-ol, m.p. 141°–142° C.

(3) Cis-6-Chloro-2,3-Dihydro-3-Hydroxy-2-[(1',2',4'-Triazolyl)-(1' or 4″)-Methyl]Benzo(b)Thiophene Add 3-bromo-7-chlorothiochroman-4-ol (30.0 gms., 0.107 mols) and 1,2,4-triazole (30.0 gms., 0.435 mols) to acetonitrile (500 ml.), and heat at reflux temperature for 30 hours. Evaporate the acetonitrile in vacuo, dissolve the resultant oily residue in chloroform (2 l.) and extract with two 2-liter portions of water. Dry the organic layer over anhydrous magnesium sulfate, filter and evaporate in vacuo. Chromatograph the resultant given on silica gel eluting consecutively with chloroform, 2% methanol/0.2% concentrated ammonium hydroxide in chloroform, 5% methanol/0.5% concentrated ammonium hydroxide in chloroform, and 8% methanol/0.8% concentrated ammonium hydroxide in chloroform. Combine like fractions and evaporate to give the less polar isomer, cis-6-chloro-2,3-dihydro-3-hydroxy-2-[(1',2',4'-triazolyl)-1'-methyl]benzo(b)thiopene (m.p. 141°-143° C. in recrystallization from acetonitrile) and the more polar isomer, cis-6-chloro-2,3-dihydro-3-hydroxy-2-[(1',2',4'-triazolyl)-4'-methyl]benzo(b)thiophene (m.p. 221°-223° C. on recrystallization from acetonitrile).

(B) In the procedure of above Preparation 1A(1-3), substitute for the starting compound, i.e., 7-chlorothiochroman-4-one, an equivalent quantity of each of the following:
(a) thiochroman-4-one,
(b) 6-chlorothiochroman-4-one,
(c) 8-chlorothiochroman-4-one,
(d) 5,7-dichlorothiochroman-4-one,
(e) 6,7-dichlorothiochroman-4-one,
(f) 6,8-dichlorothiochroman-4-one,
(g) 7-trifluoromethylthiochroman-4-one,
(h) 7-fluorothiochroman-4-one, and
(i) 8-fluorothiochroman-4-one
to obtain, respectively,
(a) cis-2,3-dihydro-3-hydroxy-2-[(1',2',4'-triazolyl)-1'-methyl]-benzo(b)thiophene,
(b) cis-5-chloro-2,3-dihydro-3-hydroxy-2-[(1',2',4'-triazolyl)-1'-methyl]benzo(b)thiophene,
(c) cis-7-chloro-2,3-dihydro-3-hydroxy-2-[(1',2',4'-triazolyl)-1'-methyl]benzo(b)thiophene,
(d) cis-4,6-dichloro-2,3-dihydro-3-hydroxy-2-[(1',2',4'-triazolyl)-1'-methyl]benzo(b)thiophene,
(e) cis-5,6-dichloro-2,3-dihydro-3-hydroxy-2-[(1',2',4'-triazolyl)-1'-methyl]benzo(b)thiophene,
(f) cis-5,7-dichloro-2,3-dihydro-3-hydroxy-2-[(1',2',4'-triazolyl)-1'-methyl]benzo(b)thiophene,
(g) cis-6-trifluoromethyl-2,3-dihydro-3-hydroxy-2-[(1',2',4'-triazolyl)-1'-methyl]benzo(b)thiophene,
(h) cis-6-fluoro-2,3-dihydro-3-hydroxy-2-[(1',2',4'-triazolyl)-1'-methyl]benzo(b)thiophene, and
(i) cis-7-fluoro-2,3-dihydro-3-hydroxy-2-[(1',2',4'-triazolyl)-1'-methyl]benzo(b)thiophene,
and the corresponding [(1',2',4'-triazolyl)-4'-methyl]-compounds.

PREPARATION 2

3-[(1',2',4'-Triazolyl)-(1' or 4')-Methyl]-Thiochroman-4-Ols (A) 7-Chloro-3-[(1',2',4'-Triazolyl)-(1' or 4')-Methyl]-Thiochroman-4ol (1) 7-Chloro-3-[(1',2',4'-Triazolyl)-(1' or 4')-methyl]-thiochroman-4-One Dissolve 1,2,4-triazole in water and add 7-chloro-3-(dimethylaminomethyl)thiochroman-4-one hydrochloride. Stir the reaction mixture overnight at room temperature, then add water and extract with chloroform. Wash the chloroform solution with water, dry over anhydrous magnesium sulfate, filter and evaporate in vacuo to a residue. Chromatograph the residue on a silica gel column eluting with chloroform. Combine the like eluates as determined by thin layer chromatography and evaporate in vacuo to a residue comprising 7-chloro-3-[(1',2',4'-triazolyl)-(1' and 4')-methyl]thiochroman-4- one.

(2) Dissolve 7-chloro-3-[(1',2',4'-triazolyl)-(1' and 4')-methyl]thiochroman-4-one in methanol, cool the solution to 0°-5° C., and add with stirring sodium borohydride. Stir the reaction mixture overnight at room temperature and evaporate in vacuo. Add water to the resultant residue and stir for 30 minutes. Filter and wash the resultant residue with water and chromatograph on a silica gel column as in Preparation 1 (A)(3). Combine the like fractions as determined by thin layer chromatography and evaporate the combined like eluates to give 4 isolated products, namely, cis-7-chloro-3-[(1',2',4'-triazolyl)-1'-methyl]thiochroman-4-ol, trans-7-chloro-3-[(1',2',4'-triazolyl)-1'-methyl]thiochroman-4-ol and the corresponding [(1',2',4'-triazolyl)-4'-methyl] compounds.

(B) In the procedure of Preparation 2A(1), substitute for the starting thiochroman compound an equivalent quantity of each of the following:
(a) 3-(dimethylaminomethyl)thiochroman-4-one hydrochloride,
(b) 6-chloro-3-(dimethylaminomethyl)thiochroman-4-one hydrochloride,
(c) 8-chloro-3-(dimethylaminomethyl)thiochroman-4-one hydrochloride,
(d) 5,7-dichloro-3-(dimethylaminomethyl)thiochroman-4-one hydrochloride,
(e) 6,7-dichloro-3-(dimethylaminomethyl)thiochroman-4-one hydrochloride,
(f) 6,8-dichloro-3-(dimethylaminomethyl)thiochroman-4-one hydrochloride, and
(g) 7-trifluoromethyl-3-(dimethylaminomethyl)thiochroman-4-one hydrochloride. to obtain, the corresponding 3-[(1', 2', 4'-triazolyl)-(1' or 4'-methyl]thiochroman-4-one derivative of each of the foregoing which, upon reaction with sodium borohydride according to the preparation of 2A(2), yields the corresponding 4-hydroxyl derivative which, upon purification via chromatography in the described manner, is separated into its respective cis and trans isomers.

PREPARATION 3

1-[(4'-1''-Acetyl4''-Piperazinyl))Phenoxyl]-2-Bromoethane

Dissolve 1-acetyl-4-(4'-hydroxyphenyl)piperazine (15.0 gms., 58.5 mmols) and potassium hydroxide (3.28 gms., 58.5 mmols) in absolute ethanol (500 ml.). Add ethylenedibromide (50.4 ml., 585 mmols) and reflux the mixture for two hours. Add another portion of potassium hydroxide (3.28 gms., 58.5 mmols) and reflux again for two hours; repeat this last step two more times. Evaporate the ethanol in vacuo. Dissolve the resultant residue in chloroform (1.1.) and extract with water (1.1.). Dry the chloroform solution over anhydrous magnesium sulfate, evaporate the chloroform, and chromatograph the resultant residue on silica gel, eluting with chloroform. Combine the like fractions as determined by thin layer chromatography and evaporate the combined eluates to give 1-[(4'-(1''-acetyl-4''-piperazinyl))phenoxy]-2-bromoethane.

EXAMPLE 1

Cis-3-Chlorothenyloxy (or chlorobenzyloxy)-2,3-Dihydro-2-[1'', 2'', 4''-Triazolylmethyl]Benzo(b)Thiophenes A. Cis-6-Chloro-3-(2'-Chloro-3'-Thenyloxy)-2,3-Dihydro-2-[(1'', 2'', 4''-Triazolyl)-1''-Methyl]Benzo(b)-Thiophenes Stir cis-6-chloro-2,3-dihydro-3-hydroxy-2-[(1', 2', 4'-triazolyl)-1'-methyl]benzo(b)thiophene (1.17 gms., 4.37 mmols), 2-chloro-3-thenylbromide (1.06 gms., 5.0 mmol) and methyl tricaprylyl ammonium chloride (0.1 gm.) in tetrahydrofuran (25 ml) and 50% sodium hydroxide (10 ml) at room temperature for one hour. Pour the reaction mixture into chloroform (500 ml.) and extract with two 500 ml. portions of water. Dry the chloroform solution over anhydrous magnesium sulfate, filter and evaporate in vacuo. Chromatograph the resultant residue on silica gel eluting with chloroform. Combine the like eluates as determined by thin layer chromatography and evaporate in vacuo to obtain cis-6-chloro-3-(2'-chloro-3'-thenyloxy)-2,3-dihydro-2-[(1", 2", 4"-triazolyl)-1"-methyl]benzo(b)thiophene, a gum.

B. In a procedure similar to that of Example 1A, instead of 2-chloro-3-thenylbromide, utilize an equivalent quantity of each of the following reagents:
 (a) 2,5-dichloro-3-thenyl bromide,
 (b) 4-chlorobenzyl chloride,
 (c) 2,4-dichlorobenzyl chloride,
 (d) chloromethylmethyl sulfide,
 (e) 3-picolyl hydrochloride,
 (f) 3-thenylbromide,
 (g) 2-chloro-5-thenylbromide, to obtain, respectively,
 (d)
  cis-6-chloro-3-(2',5'-dichloro-3'-thenyloxy)-2,3-dihydro-2-[(1",2",4"-triazolyl)-1"-methyl]benzo(b)thiophene,
  cis-6-chloro-3-(4'-chlorobenzyloxy)-2,3-dihydro-2-[(1",2", 4"-triazolyl)-1"-methyl]benzo(b)thiophene,
  cis-6-chloro-3-(2',4'-dichlorobenzyloxy)-2,3-dihydro-2-[(1",2",4"-triazolyl)-1"-methyl]benzo(b)thiophene,
  cis-6-chloro-3-(methylthiomethoxy)-2,3-dihydro-2-[(1",2",4"-triazolyl)-1"-methyl]benzo(b)thiophene,
  cis-6-chloro-3-(3'-picolyloxy)-2,3-dihydro-2-[(1",2",4"-triazolyl)-1"-methyl]benzo(b)thiophene,
  cis-6-chloro-3-(3'-thenyloxy)-2,3-dihydro-2-[(1",2",4"-triazolyl)-1"methyl]benzo(b)thiophene,
  cis-6-chloro-3-(2'-chloro-5'-thenyloxy)-2,3-dihydro-2-[(1",2",4"-triazolyl)-1"-methyl]benzo(b)thiophene, and the corresponding [(1",2"4"-triazolyl)-4"-methyl] derivatives thereof.

C. Treat each of the cis-2,3-dihydro-3-hydroxy-2-[(1',2',4'-triazolyl)-1'-methyl]benzo(b)thiophenes prepared in Preparation 1B with 2-chloro-3-thenylbromide in a manner similar to that described in Example 1A to obtain the corresponding 3-(2'-chloro-3'-thenyloxy) compound.

D. Similarly, treat each of the cis-2,3-dihydro-3-hydroxy-[(1',2',4'-triazolyl)-1'-methyl]benzo(b)thiophenes prepared in Preparation 1B with each of the seven reagents listed in Example 1B to obtain the respective 3-(2',5'-dichloro-3-thenyloxy), 3-(4'-chlorobenzyloxy), 3-(2',4'-dichlorobenzyloxy), 3-(methylthiomethoxy), 3-(3'-picolyloxy), 3-(3'-thenyloxy), and 3-(2'-chloro-5'-thenyloxy) compounds.

E. The corresponding [(1",2",4"-triazolyl)-4"-methyl] analogs may be prepared in a manner similar to that described in Example 1(A) and (B).

EXAMPLE 2

4-Substituted-3-[(1",2",4"-Triazolyl)-(1" or 4")-Methyl]Thiochromans

Treat each of the thiochroman-4-1s prepared in Preparation 2(A) and (B) with each of the reagents listed in Example 1(A) and (B) in a manner similar to that described in Example 1(A) to produce the corresponding cis and trans-4-substituted-3-[(1",2",4"-triazolyl)-(1" or 4")-methyl] thiochromans.

EXAMPLE 3

Cis-6-Chloro-3[2'-(4"-(1'''-Acetyl-4'''-Piperazinyl)Phenoxy)Ethoxy]-2,3-Dihydro-2-[(1'''',2'''',4''''-Traizolyl)-1''''-Methyl]Benzo(b)Thiophene A. Stir a mixture of the product of Preparation 1(A) and potassium hydroxide in acetone at room temperature for one hour. Add 1-((4'-(1"-acetyl-4"-piperazinyl))phenoxy)-2-bromoethane and stir overnight at room temperature. Add a second portion of potassium hydroxide and stir overnight; repeat a third time. Pour the mixture into chloroform and extract with water. Dry the chloroform solution over anhydrous magnesium sulfate and evaporate in vacuo. Chromatograph the resultant residue on silica gel eluting with 2% methanol in chloroform. Combine the like fractions as determined by thin layer chromatography and evaporate the combined like eluates to give cis-6-chloro-3-[2'-(4"-(1'''-acetyl-4'''-piperazinyl)-phenoxy)ethoxy]-2,3-dihydro-2-[(1'''',2'''',4''''-triazolyl)-1''''-methyl]benzo(b)thiophene.

B. Dissolve the product of Step A in a mixture of chloroform and methanol, acidify to pH 2–3 with hydrochloric acid/2-propanol, and evaporate to a residue comprising cis-6-chloro-3-[2'-(4"-(1'''-acetyl-4'''-piperazinyl)phenoxy)-ethoxy]-2,3-dihydro-2-[(1'''',2'''',4''''-thiazolyl)-1''''-methyl]benzo(b)thiophene dihydrochloride.

EXAMPLE 4

3-Chlorothenyloxy(or Chlorobenzyloxy)-2,3-Dihydro-2-[(1",2",4"-Triazolyl)-1"-Methyl]Benzo(b)Thiophene-1-Oxides A. 6-Chloro-3-(2',4'-Dichlorobenzyloxy)-2,3,-Dihydro-2-[(1",2",4"-Triazolyl)-1"-Methyl]Benzo(b)Thiophene-1-Oxide To a solution of the product of Example 1(A) (b) in dichloromethane cooled to 0°–5° C., add an equivalent amount of m-chloroperbenzoic acid and stir for one hour. Add sodium sulfite and stir for another 30 minutes. Add dichloromethane to the solution and extract with 10% aqueous sodium carbonate. Dry the organic phase over anhydrous magnesium sulfate and evaporate. Chromatograph the resultant residue on silica gel eluting with 5% methanol in chloroform. Combine like fractions as determined by thin layer chromotography and evaporate the combined eluates to give the title compound.

B. Treat each of the products of Examples 1, 2 and 3 in a manner similar to that of Example 4A to obtain the corresponding 1-oxides.

EXAMPLE 5

3-Chlorothenyloxy(or Chlorobenzyloxy)-2,3-Dihydro-2-[(1″,2″4″-Triazolyl)-1″-Methyl]Benzo(b)Thiophene-1,1-Dioxides A. 6-Chloro-3-(2′,4′-Dichlorobenzyloxy)-2,3-Dihydro-2-[(1″,2″,4″-Triazolyl)-1″-Methyl]Benzo(b)Thiophene-1,1-Dioxide To a solution of the product of Example 1(A)(b) in dichloromethane cooled to 0°–5° C., add twice the molar equivalent of m-chloroperbenzoic acid and stir for one hour. Warm the solution to room temperature and stir overnight. Add dichloromethane and extract with 10% aqueous sodium carbonate. Dry the organic phase over anhydrous magnesium sulfate and evaporate to give a residue comprising the title compound.

B. Treat each of the products of Example 1, 2 and 3 in a manner similar to that of Example 5A to obtain the corresponding 1,1-dioxides.

EXAMPLE 6

Cis-6-Chloro-3-(2′-Chloro-3′-Thenyloxy)-2,3-Dihydro-2-[(1″,2″,4″-Triazolyl)-1″-Methyl]Benzo(b)Thiophene Hydrochloride Dissolve cis-6-chloro-3-(2′-chloro-3′-thenyloxy)-2,3-dihydro-2-[(1″,2″,4″-triazolyl)-1″-methyl]benzo(b)thiophene (2.0 gms.) in anhydrous ether (400 ml.). Add dropwise a saturated solution of HCl gas in 2-propanol until precipitation is complete, filter and dry the resultant residue to obtain the title compound.

The products of Example 1 may be treated in a similar manner to obtain the corresponding hydrochloride acid addition salts.

We claim:

1. A compound selected from the group consisting of a compound defined by formula:

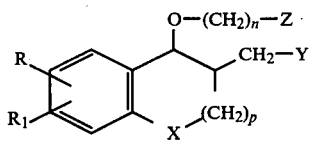

wherein
n is 0 to 4;
p is 0 or 1;
R and $R_1$ are independently H, lower alkyl, halogen, halogenated lower alkyl, nitro, or amino;
X is sulfur, sulfinyl, or sulfonyl;
Y is 1,2,4-triazolyl or 1,2,4-triazolyl substituted by lower alkyl or aryl, said aryl being a member selected from the group consisting of phenyl, halophenyl, and loweralkylphenyl;
Z is a member selected from the group consisting of alkyl of 1 to 10 carbons, alkenyl of 3 to 10 carbons, alkynyl of 3 to 10 carbons, cycloalkyl of 3 to 6 carbons, and heterocyclic aromatic groups selected from the group consisting of 2-thienyl, 3-thienyl, pyridyl, quinolyl, thiazolyl and furanyl, and the lower alkyl and halogen substituted derivatives thereof, provided that when n is 0, Z is not 1-alkynyl; and where n is 1 to 4, Z is also a member selected from the group consisting of phenyl, phenyl substituted by lower alkyl, halogen, or N-(N′-lower alkanoylpiperazine), alkoxy of 1 to 10 carbons, alkylthio of 1 to 10 carbons, aryloxy, and arylthio, wherein said aryl is a member selected from the group consisting of phenyl, halophenyl, and lower alkyl phenyl;
and the pharmaceutically acceptable acid addition salts thereof.

2. A compound of claim 1 wherein X is S.

3. A compound of claim 1 wherein p is 0.

4. A compound of claim 1 wherein Y is 1,2,4-triazolyl.

5. A compound of claim 1 wherein Z is a heterocyclic aromatic group.

6. A compound of claim 2 wherein p is 0.

7. A compound of claim 2 wherein p is 0 and Y is 1,2,4-triazolyl.

8. A compound of claim 7 wherein Z is a heterocyclic aromatic group.

9. A compound of claim 8 wherein R is H, $R_1$ is 6-chloro, n is 1, and Z is 2-chloro-3-thienyl, said compound being cis-6-chloro-3-(2′-chloro-3′-thenyloxy)-2,3-dihydro-2-[(1″,2″,4″-triazolyl)-1″-methyl]benzo(b)thiophene.

10. A composition useful for inhibiting the growth of fungi, bacteria or protozoa which comprises an antifungally, antibacterially, or antiprotozoally effective amount of a compound of claim 1 in admixture with a carrier.

11. The composition of claim 10 suitable for pharmaceutical use wherein the carrier is a pharmaceutically acceptable, non-toxic carrier.

12. The composition of claim 11 which comprises an antifungally, antibacterially, or antiprotozoally effective amount of the compound of claim 1 together with a pharmaceutically acceptable non-toxic carrier.

13. A method of inhibiting the growth of fungi, bacteria, or protozoa which comprises subjecting a host object containing or subject to attack by fungi, bacteria, or protozoa to an antifungally, antibacterially, or antiprotozoally effective amount of a compound of claim 1.

14. The method of claim 13 which comprises administering to the host an antifungally, antibacterially, or antiprotozoally effective amount of the compound of claim 8 together with a pharmaceutically acceptable non-toxic carrier.

15. Compounds represented by the formula

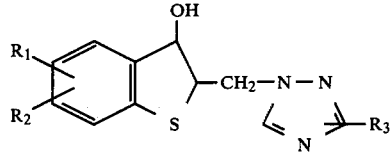

wherein
R and $R_1$ are independently hydrogen, lower alkyl, halogen, halogenated lower alkyl, nitro, or amino; and
$R_3$ is hydrogen, lower alkyl or aryl, said aryl being a member selected from the group consisting of phenyl, halophenyl, and loweralkylphenyl.

* * * * *